United States Patent
Jurisch et al.

(10) Patent No.: US 11,344,857 B2
(45) Date of Patent: May 31, 2022

(54) MICROCAPSULES

(71) Applicants: Symrise AG, Holzminden (DE); PAPIERFABRIK AUGUST KOEHLER SE, Oberkirch (DE)

(72) Inventors: Claus Jurisch, Offenburg (DE); Michael Horn, Offenburg (DE); Claudia Meier, Lichtenau (DE); Ralf Bertram, Holzminden (DE); Patrick Ott, Holzminden (DE)

(73) Assignees: Symrise AG, Holzminden (DE); Papierfabrik August Koehler SE, Oberkirch (DE)

(*) Notice: Subject to any disclaimer, the term of this patent is extended or adjusted under 35 U.S.C. 154(b) by 54 days.

(21) Appl. No.: 16/472,413

(22) PCT Filed: Jan. 25, 2017

(86) PCT No.: PCT/EP2017/051481
§ 371 (c)(1),
(2) Date: Jun. 21, 2019

(87) PCT Pub. No.: WO2018/114056
PCT Pub. Date: Jun. 28, 2018

(65) Prior Publication Data
US 2019/0358603 A1    Nov. 28, 2019

(30) Foreign Application Priority Data
Dec. 22, 2016    (WO) ................. PCT/EP2016/082399

(51) Int. Cl.
*B01J 13/18* (2006.01)
*B01J 13/04* (2006.01)
*B01J 13/20* (2006.01)

(52) U.S. Cl.
CPC .......... *B01J 13/185* (2013.01); *B01J 13/043* (2013.01); *B01J 13/206* (2013.01)

(58) Field of Classification Search
CPC ... B01J 1/185; B01J 1/043; B01J 1/206; B01J 1/14; C11D 3/505; A61K 8/11; A61K 9/50; C10N 2050/12; C09B 67/0097; A01N 25/28; F28D 20/023
USPC ................. 424/408, 490; 264/4.7; 512/4; 428/402.2
See application file for complete search history.

(56) References Cited

U.S. PATENT DOCUMENTS

| | | | |
|---|---|---|---|
| 2003/0202999 A1* | 10/2003 | Klassen | A01N 25/18 424/417 |
| 2004/0195711 A1 | 10/2004 | Hayashi et al. | |
| 2012/0157315 A1* | 6/2012 | Casana Giner | A01N 47/28 504/359 |
| 2015/0210965 A1* | 7/2015 | Bertram | A61Q 19/007 424/401 |
| 2016/0177241 A1* | 6/2016 | Brundel | C11D 3/30 512/4 |
| 2017/0273877 A1* | 9/2017 | Sasaki | A61Q 13/00 |

FOREIGN PATENT DOCUMENTS

WO    2006/050638 A1    5/2006

OTHER PUBLICATIONS

Database WPI Week 199118, Thomson Scientific, London, GB; AN 1991-129339, XP00277353 & JP H03-68948A, Mar. 25, 1991.
Database WPI Week 199012, Thomson Scientific, London, GB; AN 1990-088101, XP002773354 & JP H02-42444A, Feb. 13, 1990.

* cited by examiner

*Primary Examiner* — Tri V Nguyen
(74) *Attorney, Agent, or Firm* — Dilworth & Barrese, LLP

(57) ABSTRACT

The invention relates to the field of capsules having a high load of active ingredients or substances, to the use thereof in cosmetic preparations, pharmaceuticals, household products, cleaning agents and technical compositions, e.g. adhesive and coating compositions, and to the manufacturing of the capsules.

9 Claims, No Drawings

MICROCAPSULES

FIELD OF THE INVENTION

The invention relates to the field of capsules having a high active ingredient or active substance loading, and to the use thereof in cosmetic formulations, pharmaceutical compositions, domestic and cleaning products and industrial compositions, for example adhesive and coating compositions, paints, coatings, binders, materials such as plastics, paper, textiles, lubricants, building materials, dyes, organic and inorganic powders, pigment dispersions, agrochemicals, phase transition materials, flame retardants and the production of capsules.

STATE OF THE ART

Encapsulations of active ingredients, especially of aromas or fragrances or active cosmetic or pharmaceutical ingredients or agrochemicals, are prior art and often offer the possibility of stabilizing the encapsulated material and protecting it from reactions with the medium in order thus to maintain the effect of the active ingredient and release it in a controlled manner.

As well as macroscopic particles having diameters in the range of up to 1 cm, microcapsules are of particular interest. This is understood by the person skilled in the art to mean spherical particles having a diameter in the range from about 0.0001 to about 5 and preferably 0.005 to 0.5 mm which have at least one solid or liquid core encased by at least one continuous shell. More specifically, they are polymer-encased, finely dispersed liquid or solid phases, in the production of which the polymers, after emulsification and, for example, coacervation or interfacial polymerization, are precipitated on the material to be encased.

The shell of such microcapsules may consist of natural, semisynthetic or synthetic materials.

The encapsulation of active ingredients using gelatin and polysaccharides, specifically gum arabic, is the subject of numerous property rights. The oldest publications are from 1958 to 1974, namely U.S. Pat. No. 3,041,288; JP 50 027826 A and JP 51 013387 A.

Examples of prior art microcapsules are the following commercial products (the shell material is stated in brackets in each case): Hallcrest microcapsules (gelatin, gum arabic), Coletica Thalaspheres (maritime collagen), Lipotec millicapsules (alginic acid, agar-agar), Induchem Unispheres (lactose, microcrystalline cellulose, hydroxypropyl methylcellulose); Unicerin C30 (lactose, microcrystalline cellulose, hydroxypropyl methylcellulose), Kobo Glycospheres (modified starch, fatty acid esters, phospholipids), Softspheres (modified agar-agar) and Kuhs Probiol Nanospheres (phospholipids), and Primaspheres and Primasponges (chitosan, alginates) and Primasys (phospholipids). And also capsules made from synthetic polymers Micronal® (BASF), 500 and 560 microcapsules (Koehler SE), Folco Smartcaps®, Enfinit™, Ensensa™

The conventional encapsulation methods in the foods sector are usually water-based and hence also give solely water-soluble particles. But since virtually all foods contain water, the customary technologies, for example spray drying, spray pelletization or extrusion, can deliver the required release only to a very limited degree, if at all, when the food is heated or on consumption.

The substances and active ingredients enclosed in microcapsules are generally referred to as core material.

By the selection of suitable wall materials, it is possible to influence the physical and chemical properties of microcapsules in a controlled manner. The handling and storage of the products in powder form makes them extremely user-friendly.

The use of various wall and core materials results in a variety of possible uses.

Examples of ingredients and fields of use of microcapsules lie in the sectors of fragrances (fragrance marketing, fragrant coatings), aromas, dyes, for example in carbon copy papers (first industrial use of microencapsulation, 1953 patent), luminous paints, oils and lubricants (lubrication under mechanical stress), adhesives (bonding under pressure), solvents, detergents, disinfectants, preservatives, washing compositions (enzymes), pharmaceuticals, food supplements (delayed release, retardation), pesticides (better handling which is less hazardous to health), flame retardants, optical brighteners, reactive plastics (epoxy resins, polyurethanes) and self-healing surface coatings and solid materials, drilling aids, latent heat stores, corrosion protection, process auxiliaries such as catalysts, crosslinkers or rheology aids, defoamers and surfactants.

A problem with the prior art particles is often the capsule shell. Especially when a high loading of aromas or fragrances is to be attained, aromas or fragrances frequently diffuse out of the capsule shell before they are employed in the case of storage in extractive use formulations (for example surfactant solutions).

It was therefore an object of the present invention to produce stable capsules that contain active ingredients or substances and have a storage stability of at least 8 weeks in the use formulation. It was a further object of the present invention to develop capsules that enable variable loading, and also enable a high active ingredient loading, such that the capsules can have the broadest possible employability, meaning that the capsules can encapsulate active ingredients from different sectors such as washing and cleaning compositions, adhesives, coating compositions, agrochemicals, but also cosmetic and pharmaceutical sectors, and can be incorporated correspondingly in a wide variety of different products.

DESCRIPTION OF THE INVENTION

The invention firstly provides microcapsules comprising or consisting of
(a) a core
  (a1) containing at least one, two or more than two active ingredients,
  (a2) at least one of which is liquid at 25° C., and
(b) a shell,
  (b1) wherein the wall material of the shell is formed from one or more polymers and at least one at least five-membered cyclic aromatic or heteroaromatic component containing at least one hydroxyl function and at least one amino function,
  (b2) where the two groups here are separated from one another by at least one unsubstituted atom of the aromatic or heteroaromatic system.

The invention secondly relates to microcapsules comprising or consisting of
(a) a core containing at least one, two or more than two active ingredients, and
(b) a shell,
wherein the wall material of the shell is formed from one or more amino resins that are formed from (i) at least one urea derivative or melamine derivative, and a carbonyl compound, and
(ii) at least one aminophenol component of the formula (Ia) and/or (Ib),

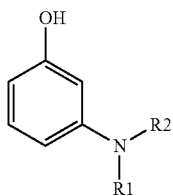

(Ia)

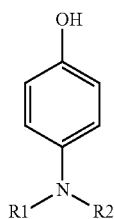

(Ib)

in which R1 and R2 independently represent hydrogen, methyl or ethyl.

It has been found that, surprisingly, microcapsules wherein the wall material has been formed from at least one aminophenol component (Ia) or (Ib) or mixtures thereof are particularly storage-stable in surfactant-containing use formulations, for example.

A further advantage of the capsules of the invention is their stability, which enables use of the capsules in a wide variety of different sectors in order to introduce the desired different active ingredients and active substances, according to the use requirement, into the corresponding medium and to release them when required.

Active Ingredients for Encapsulation

The selection of active ingredients that are to be encapsulated is therefore uncritical and is guided essentially solely by what end use is to be pursued. These may, for example, also be dyes. Preference is given to encapsulating active ingredients and constituents from the sectors of washing and cleaning compositions, adhesives, coating compositions, for example paints and coatings, binders, materials such as plastics, paper, textiles, lubricants, building materials, dyes, organic and inorganic powders, pigment dispersions, phase transition materials, flame retardants, agrochemicals, but also materials from cosmetic and pharmaceutical sectors.

The microcapsules of the invention preferably contain active ingredients, or preference is given to encapsulating active ingredients by the present process, that are selected from the group consisting of: fragrances, perfume oils, vitamins, minerals, antioxidants, anthocyanins, coenzynne10, adhesives, mineral oils, waxes and greases, biocides, fungicides, herbicides, pesticides, insecticides, fertilizers, disperse dyes and dye solutions or monomers for synthesis of plastics.

Preference is given to fragrances or perfume oils.

Perfume Oils

Perfume oils include mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamon, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also useful are animal raw materials, for example civet and castoreum. Typical synthetic odorant compounds are products of the ester, ether, aldehyde, ketone, alcohol and hydrocarbon type. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isonnethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams. However, preference is given to using mixtures of different odorants which together produce a pleasing fragrance note. Essential oils of relatively low volatility, which are usually used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnannaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-dannascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat alone or in mixtures.

In addition, a further preferred embodiment of the present invention is that of capsules comprising the aforementioned active ingredients or active substances, but also comprising the constituents or active ingredients or active substances mentioned below for cosmetic and washing and cleaning compositions.

Production Methods

The invention further relates to a process for producing microcapsules, comprising the following steps:
A) providing a pre-emulsion comprising stabilizers and wall formers, and the active ingredients to be encapsulated;
B) initiating the condensation by altering temperature and/or pH, optionally by adding alcohol or salting-out;
C) post-hardening by
   (c1) adding a dispersion containing at least one urea derivative or melamine derivative or
   (c2) a corresponding precondensate of urea and/or melamine and an aldehyde, and adding aminophenol components (Ia) and/or (Ib), preferably in aqueous form, at temperatures of 50° C. to 100° C.;
D) adding urea, preferably in aqueous form or in solid form;
E) cooling the reaction mixture; and optionally
F) spray-drying or spray-pelletizing the capsules obtained.

It has been found that, surprisingly, by means of the present production process, particularly storage-stable microcapsules additionally containing little formaldehyde are obtained. The concentration of free aldehydes here is preferably below 400 ppm, more preferably below 300 ppm, most preferably below 100 ppm.

The microcapsules thus produced can accordingly be incorporated in different products.

Accordingly, a preferred execution is a process of the invention wherein less than 5% by weight of formaldehyde forms in the production of the microcapsules, based on the overall composition in the production. The free formaldehyde limit by virtue of the present production process is preferably in the range from 0.001% to 5% by weight, preferably from 0.01% to 3% by weight, more preferably from 0.01% to 1% by weight, based on the overall composition of a microcapsule.

Encapsulation

Wall formers and stabilizers are dissolved in water with stirring. The solution is adjusted to a temperature in the range from 10 to 100° C., preferably from 30 to 90° C. Thereafter, the core material is added and emulsified in this mixture. Smaller capsules are formed here with higher stirrer output and longer reaction time, and vice versa. Useful further additives here include acids such as acetic acid, formic acid, citric acid or else mineral acids, for example hydrochloric or sulfuric acid, with which the pH of the solution is kept within the acidic range at about 3 to 5. Since the mixtures can have a tendency to evolve foam, it is possible to add commercial silicone defoamers, for example.

Curing or Crosslinking of the Capsules

The capsules still have a flexible shell that does not have any notable stability and therefore does not attain the desired diffusion density either. For this purpose, curing or crosslinking of the shell is conducted.

For curing, an aqueous melamine dispersion is added and stirred at about 60 to about 70° C. for about 30 min. to about 1 h. This is followed by heating to about 80° C. and addition of an aqueous aminophenol solution and stirring at about 80° C. to about 90° C. for about 30 min. to about 1 h.

Subsequently, a urea derivative is added in the form of a solution or in solid form and stirred again at about 80° C. to about 90° C. for about 30 min. to about 1 h. This is followed by cooling.

The capsule dispersions of the invention preferably have a very high active ingredient loading that can be varied according to the use requirement. Preferably, the capsules of the invention accordingly have an active ingredient loading of 10% to 60% by weight, preferably of 20% to 45% by weight, most preferably of 25% to 40% by weight, based on the overall composition of the capsule dispersion. The active ingredient or active substance loading is dependent on the final application of the capsules and accordingly varies according to the field of use. The loading can be correspondingly varied and adjusted according to the use requirement.

The aforementioned loading ranges should be regarded as possible example parameters, and are not intended to constitute any restriction in respect of the loadings producible.

Preferably, the capsules of the invention may have an average diameter of 1 to 1000 μm, preferably of 2 to 80 μm. The capsule size may be varied and adjusted correspondingly according to the use requirement. Accordingly, the aforementioned capsule size ranges should be regarded as possible example parameters, and are not intended to constitute any restriction in respect of the capsule sizes producible.

In the present application, the term "capsule" is equated to the term "particle". The two terms are equivalent and should be regarded as being interchangeable.

In addition, it is possible to choose a wall material that forms as a second shell around the present microcapsules. It may be constructed from one or more polymers selected from natural, semisynthetic, synthetic polymer material or mixtures thereof.

Natural shell materials are, for example, gum arabic, agar-agar, agarose, maltodextrins, alginic acid or salts thereof, e.g. sodium or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes.

Semisynthetic shell materials include chemically modified celluloses, especially cellulose esters and ethers, e.g. cellulose acetate, ethyl cellulose, hydroxypropyl cellulose, hydroxypropyl methylcellulose and carboxymethylcellulose, and starch derivatives, especially starch ethers and esters. Synthetic shell materials are, for example, polymers such as polyacrylates, polyamides, polyvinyl alcohol, amino resins, phenolic resins or polyvinylpyrrolidone.

The urea derivative or melamine derivative for formation of the present microcapsules is preferably selected from 2,4,6-triamino-1,3,5-triazine (melamine) or tetrahydroimidazo[4,5-d]imidazole-2,5(1H,3H)-dione (glycoluril), guanamines such as benzoguanamine and acetoguanamine, bisguanamines such as adipo- and glutaroguanamine or mixtures thereof.

The aminophenol component used in the curing of the present microcapsules is preferably the compound (Ia) or (Ib) or a mixture of (Ia) and (Ib), where, in the case of a mixture of (Ia) and (Ib), the ratio of components (Ia):(Ib) is from 10:1 to 1:5. The aminophenol component for the production of the present microcapsules is preferably 3-aminophenol.

INDUSTRIAL APPLICABILITY

One advantage of the capsules of the invention in which the urea derivative or melamine derivative and the aminophenol components mentioned are used to form the present microcapsules is their good retention capacity, meaning that the capsules of the invention have at least 30% to 70%, preferably at least 40% to 60%, retention of the capsule contents after storage in a surfactant-containing use formulation for 8 weeks at a temperature of 45° C., preferably 20% to 60%, preferably 30% to 50%, after storage for 12 weeks.

Preferably, the capsules of the invention are used to produce pharmaceutical or cosmetic products or washing and cleaning compositions. Preference is given to pharmaceutical and cosmetic products, especially suitable for use on the skin. Preference is given here both to cosmetic products and to pharmaceutical compositions in the form of ointments, creams, lotions, gels and pastes and sprays.

An ointment, cream, lotion, gel and paste is preferably understood to mean a semisolid spreadable formulation suitable for application to the skin.

Such formulations may be based, for example, on an aqueous (hydrophilic) and an oily or fatty (lipophilic) component, one of which is distributed in the manner of an emulsion in the other.

They may likewise be hydrophilic creams of the O/W type or lipophilic creams of the W/O type. In addition, there are creams that cannot be assigned unambiguously to the O/W type or to the W/O type that consist of coherently interdistributed lipophilic and hydrophilic phases of the gel type (amphiphilic creams). Structures of a multiple emulsion of the W/O/W emulsion type are also possible. The inner face here is again in the form of an emulsion. Ultrasmall water droplets are once again incorporated into the inner oil phase.

This type of emulsion is intended to combine the advantages of W/O emulsions and O/W emulsions in one.

Further formulations are preferably ointments, which is generally a semisolid formulation of homogeneous appearance and is suitable for application on the skin (for example as wound ointment) or on the mucus membranes. Ointments usually serve for local administration of active ingredient or for care and protection of the skin or mucous membranes. An ointment preferably consists of a hydrophobic or hydrophilic base composed of natural or synthetic substances and may be a monophasic system (e.g. Vaseline) or polyphasic system (e.g. water-in-oil).

In addition, the microcapsules of the invention may be used for the production of, for example, perfume extracts, eaux de parfum, eaux de toilette, aftershaves, eaux de cologne, pre-shave products, splash colognes and perfumed freshen-up wipes, and the perfuming of acidic, alkaline and neutral cleaning compositions, such as floor cleaners, window glass cleaners, dishwashing products, bath and sanitary cleaners, scouring cream, solid and liquid toilet cleaners, carpet cleaners in powder and foam form, liquid washing compositions, pulverulent washing compositions, laundry pre-treatment compositions such as bleaches, soaking compositions and stain removers, fabric softeners, washing soaps, washing tablets, disinfectants, surface disinfectants, and of air fresheners in liquid form, of the gel type or in a form applied to a solid carrier, aerosol sprays, waxes and polishes, such as furniture polishes, floor waxes, shoe creams, and personal care products, for example solid and liquid soaps, shower gels, shampoos, shaving soaps, shaving foams, bath oils, cosmetic emulsions of the oil-in-water, of the water-in-oil and of the water-in-oil-in-water type, for example skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, haircare products, for example hairsprays, hair gels, setting hair lotions, hair rinses, permanent and semipermanent hair colorants, hair-shaping products such as cold waves and hair-straightening products, hair tonics, hair creams and hair lotions, deodorants and antiperspirants, for example underarm sprays, roll-ons, deodorant sticks, deodorant creams, decorative cosmetics products, for example eyeshadows, nail varnishes, make-up products, lipsticks and mascara, and also candles, lamp oils, joss sticks, insecticides, repellents and propellants.

Preference is given to using the capsules of the invention in washing and cleaning compositions (abbreviated to WCCs). WCCs in the context of the present invention may be in solid form as powders, granules, tablets and the like, or else in liquid, gel or paste form. These are preferably washing compositions suitable both for manual or machine washing, especially of textiles. They may also be washing or cleaning compositions for the industrial sector or for the domestic sector. Cleaning compositions may also be used, for example, for cleaning of hard surfaces. These may, for example, be dishwashing detergents that are used for manual or machine washing of dishware. They may also be conventional industrial or domestic cleaners with which hard surfaces such as furniture surfaces, slabs, tiles, walls and floor coverings are cleaned. Possible hard surfaces, as well as dishware, also include all other hard surfaces, especially made of glass, ceramic, plastic or metal, in the domestic and commercial setting.

The WCCs may include further customary constituents, for example surfactants, builders, bleaches, bleach activators, thickeners, enzymes, electrolytes, pH modifiers, dyes and fragrances, foam inhibitors, antiredeposition agents, optical brighteners, graying inhibitors, anticrease agents, active antimicrobial ingredients, preservatives, antioxidants, antistats, UV adsorbers, heavy metal complexing agents and the like.

A further aspect of the present invention is the use of aminophenol components of the formula (Ia) and/or (Ia)

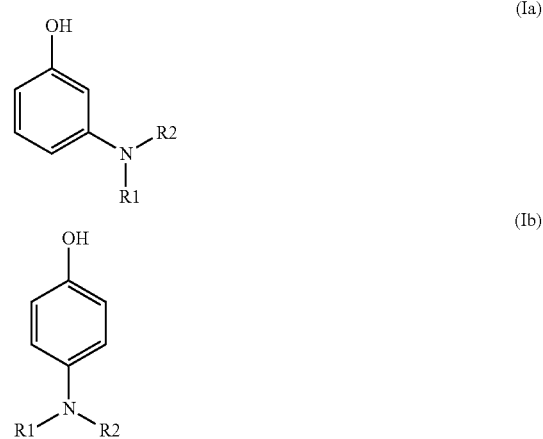

for production of microcapsules for consolidation of the wall material of the microcapsules.

Preference is given to using the compound (Ia) or (Ib) or a mixture of (Ia) and (Ib), where, in the case of a mixture of (Ia) and (Ib), the ratio of components (Ia):(Ib) is from 10:1 to 1:5. Preference is given to using 3-aminophenol as aminophenol component.

The preferred use of the aminophenol component in the production process for microcapsules is that these are added in the post-hardening step.

The use of the aminophenol components of the formula (Ia) and/or (Ia) during the post-hardening surprisingly led to stable capsule shells. By comparison 3-aminophenol had the best stability, in particular in relation to the retention capacity of different active ingredients, especially fragrances, in the capsule shell.

Accordingly, the invention further provides for the use of aminophenol components of the formula (Ia) and/or (Ia)

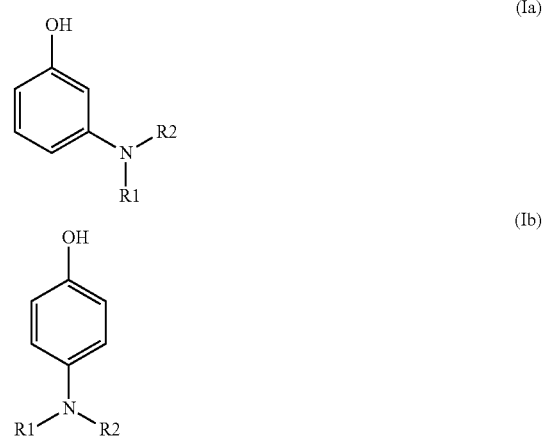

for increasing the stability of the shell of microcapsules, especially for increasing the retention capacity of active ingredients in the capsule, preferably of fragrances in microcapsules.

The present invention further provides washing and cleaning compositions, cosmetic formulations (especially personal care compositions), perfume compositions, agrochemicals or adhesives that comprise the microcapsules of the invention, and the use of the microcapsules for production of these products.

Washing and Cleaning Compositions

Builders

Builders which may be present in the liquid washing and cleaning compositions and may be encapsulated are especially silicates, aluminum silicates (especially zeolites), carbonates, organic cobuilders, phosphates, salts of organic di- and polycarboxylic acids, and mixtures of these substances.

Suitable crystalline layered sodium silicates have the general formula $NaMSi_xO_{2x+1}*H_2O$ where M is sodium or hydrogen, x is a number from 1.9 to 4 and y is a number from 0 to 20, and preferred values of x are 2, 3 or 4. Preferred crystalline sheet silicates of the formula specified are those in which M is sodium and x assumes the values of 2 or 3. In particular, preference is given both to beta- and delta-sodium disilicates $Na_2Si_2O_5*yO_2O$.

It is also possible to use amorphous sodium silicates having an $Na_2O:SiO_2$ modulus of 1:2 to 1:3.3, preferably from 1:2 to 1:2.8 and especially from 1:2 to 1:2.6, which have delayed dissolution and secondary detergency properties. The dissolution delay compared with conventional amorphous sodium silicates may have been brought about here in various ways, for example as result of surface treatment, compounding, compaction/compression or as a result of overdrying. In the context of this invention, the term "amorphous" is also understood to mean "X-ray-amorphous". This means that, in X-ray diffraction experiments, the silicates do not give any sharp X-ray reflections, as are typical for crystalline substances, but at most give one or more maxima of the scattered X-ray radiation, which have a width of several degree units of the diffraction angle. It can, however, quite possibly even lead to particularly good builder properties if the silicate particles in electron diffraction experiments give indistinct or even sharp diffraction maxima. This should be interpreted in such a way that the products have microcrystalline regions of tens to a few hundreds of nm in size, preference being given to values of up to a maximum of 50 nm and especially up to a maximum of 20 nm. These are called X-ray amorphous silicates and likewise have a dissolution delay compared with conventional waterglasses. Particular preference is given to compressed/compacted amorphous silicates, compounded amorphous silicates and overdried X-ray-amorphous silicates.

A usable finely crystalline, synthetic zeolite containing bound water is preferably zeolite A and/or P. As zeolite P, particular preference is given to zeolite MAP™ (commercial product of Crosfield). Also suitable, however, are zeolite X and mixtures of A, X and/or P. Also commercially available and usable with preference in the context of the present invention is for example a cocrystallizate of zeolite X and zeolite A (about 80% by weight of zeolite X), which is sold by SASOL under the trade name VEGOBOND AX® and can be described by the formula

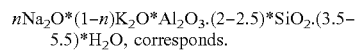

nNa₂O*(1−n)K₂O*Al₂O₃.(2−2.5)*SiO₂.(3.5– 5.5)*H₂O, corresponds.

The zeolite can be used in the form of a spray-dried powder or else of an undried, stabilized suspension that is still wet from its preparation. If the zeolite is used in the form of a suspension, this may comprise small additives of nonionic surfactants as stabilizers, for example 1% to 3% by weight, based on zeolite, of ethoxylated $C_{12}$-$C_{18}$ fatty alcohols having 2 to 5 ethylene oxide groups, $C_{12}$-$C_{14}$ fatty alcohols having 4 to 5 ethylene oxide groups or ethoxylated isotridecanols. Suitable zeolites have a mean particle size of less than 10 μm (volume distribution; measurement method: Coulter counter) and contain preferably 18% to 22% by weight, especially 20% to 22% by weight, of bound water.

It is of course also possible to use the commonly known phosphates as builder substances, unless such a use should be avoided for environmental reasons. Of particular suitability are the sodium salts of the orthophosphates, the pyrophosphates and especially the tripolyphosphates.

Suitable builders are organic cobuilders, especially polycarboxylates/polycarboxylic acids, polymeric polycarboxylates, aspartic acid, polyacetals, dextrins, and phosphonates.

Polymeric polycarboxylates are for example the alkali metal salts of polyacrylic acid or of polymethacrylic acid, for example those having a relative molecular mass of 500 to 70 000 g/mol. The molar masses stated for polymeric polycarboxylates in the context of this specification are weight-average molar masses Mw of the particular acid form, which have been determined in principle by means of gel permeation chromatography (GPC), using a UV detector. The measurement was effected here against an external polyacrylic acid standard, which gives realistic molar mass values because of its structural similarity with the polymers examined. These data are distinctly different from the molar mass data where polystyrenesulfonic acids are used as the standard. The molar masses measured against polystyrenesulfonic acids are generally distinctly higher than the molar masses stated in this specification.

Suitable polymers are especially polyacrylates, which preferably have a molecular mass of 2000 to 20 000 g/mol. Because of their superior solubility, preference may be given in turn to the short-chain polyacrylates having molar masses of 2000 to 10 000 g/mol, and more preferably of 3000 to 5000 g/mol, from this group.

Also suitable are copolymeric polycarboxylates, especially those of acrylic acid with methacrylic acid and of acrylic acid or methacrylic acid with maleic acid. Particularly suitable copolymers have been found to be those of acrylic acid with maleic acid which contain 50% to 90% by weight of acrylic acid and 50% to 10% by weight of maleic acid. The relative molecular mass thereof, based on free acids, is generally 2000 to 70 000 g/mol, preferably 20 000 to 50 000 g/mol and especially 30 000 to 40 000 g/mol.

Also especially preferred are biodegradable polymers of more than two different monomer units, for example those which contain, as monomers, salts of acrylic acid and of maleic acid, and also vinyl alcohol or vinyl alcohol derivatives, or those which contain, as monomers, salts of acrylic acid and of 2-alkylallylsulfonic acid, and sugar derivatives.

Further preferred copolymers are those which include, as monomers, preferably acrolein and acrylic acid/acrylic acid salts or acrolein and vinyl acetate.

Further preferred builder substances likewise include polymeric aminodicarboxylic acids, salts thereof or precursor substances thereof. Particular preference is given to polyaspartic acids and salts and derivatives thereof which, as well as cobuilder properties, also have a bleach-stabilizing effect.

Further suitable builder substances are polyacetals which can be obtained by reacting dialdehydes with polyolcarboxylic acids having 5 to 7 carbon atoms and at least 3 hydroxyl groups. Preferred polyacetals are obtained from dialdehydes such as glyoxal, glutaraldehyde, terephthalaldehyde, and mixtures thereof and from polyolcarboxylic acids such as gluconic acid and/or glucoheptonic acid.

Further suitable organic builder substances are dextrins, for example oligomers and polymers of carbohydrates which can be obtained by partial hydrolysis of starches. The hydrolysis can be conducted by customary processes, for example acid- or enzyme-catalyzed processes. The hydrolysis products are preferably those having average molar masses in the range from 400 to 500 000 g/mol. Preference is given to a polysaccharide having a dextrose equivalent (DE) in the range from 0.5 to 40, especially from 2 to 30, DE being a customary measure for the reducing action of a polysaccharide compared to dextrose, which has a DE of 100. It is possible to use either maltodextrins with a DE between 3 and 20 and dry glucose syrups having a DE between 20 and 37 or what are called yellow dextrins and white dextrins having higher molar masses in the range from 2000 to 30 000 g/mol.

The oxidized derivatives of such dextrins are the reaction products thereof with oxidizing agents, which are able to oxidize at least one alcohol function of the saccharide ring to the carboxylic acid function. A product oxidized at C6 of the saccharide ring may be particularly advantageous.

A preferred dextrin is described in British patent application GB 9,419,091 B1. The oxidized derivatives of such dextrins are their reaction products with oxidizing agents which are able to oxidize at least one alcohol function of the saccharide ring to the carboxylic acid function. Oxidized dextrins of this type and processes for preparation thereof are known for example from European patent applications EP 032202 A, EP 0427349 A, EP 0472042 A and EP 0542496 A, and international patent applications WO 1992/018542 A, WO 1993/008251 A, WO 1994/028030 A, WO 1995/007303 A, WO 1995/012619 A and WO 1995/020608 A. A product oxidized at $C_6$ of the saccharide ring may be particularly advantageous.

Further suitable cobuilders are also oxydisuccinates and other derivatives of disuccinates, preferably ethylenediamine disuccinate. Ethylenediamine N,N'-disuccinate (EDDS) is preferably used in the form of its sodium or magnesium salts. Preference is further given in this connection also to glycerol disuccinates and glycerol trisuccinates, as described for example in US patent specifications U.S. Pat. Nos. 4,524,009, 4,639,325, in European patent application EP 0150930 A and Japanese patent application JP 1993/339896 A.

Further usable organic cobuilders are, for example, acetylated hydroxycarboxylic acids and salts thereof, which may optionally also be in lactone form and which contain at least 4 carbon atoms and at least one hydroxyl group, and not more than two acid groups. Cobuilders of this kind are described for example in international patent application WO 1995/020029 A.

A further substance class having cobuilder properties is that of the phosphonates. These are especially hydroxyalkane- and aminoalkanephosphonates. Among the hydroxyalkanephosphonates, 1-hydroxyethane-1,1-diphosphonate (HEDP) is of particular significance as cobuilder. It is preferably used as the sodium salt, with the disodium salt giving a neutral reaction and the tetrasodium salt giving an alkaline (pH 9) reaction. Useful aminoalkanephosphonates are preferably ethylenediaminetetramethylenephosphonate (EDTMP), diethylenetriaminepentamethylenephosphonate (DTPMP), and higher homologs thereof. They are preferably used in the form of the neutral-reacting sodium salts, e.g. as the hexasodium salt of EDTMP or as the hepta- and octasodium salt of DTPMP. The builder used here from the class of phosphonates is preferably HEDP. The aminoalkanephosphonates, moreover, have a marked heavy metal binding capacity. Accordingly, it may be preferable, especially if the washing and cleaning compositions also comprise bleach, to use aminoalkanephosphonates, especially DTPMP, or to use mixtures of the stated phosphonates for production of the compositions.

In addition, it is possible to use all compounds which are able to form complexes with alkaline earth metal ions as cobuilders.

Bleaches and Bleach Catalysts

Bleaches that can be encapsulated include, for example, sodium percarbonate, peroxypyrophosphates, citrate perhydrates, and also $H_2O_2$-producing peracidic salts or peracids, such as perbenzoates, peroxophthalates, diperazelaic acid, phthaloimino peracid or diperdodecanedioic acid. In order to achieve an improved bleaching action in the case of washing at temperatures of 60° C. and below, bleach activators can be incorporated into the washing and cleaning compositions. Bleach activators used may be compounds which, under perhydrolysis conditions, produce aliphatic peroxocarboxylic acids having preferably 1 to 10 carbon atoms, especially 2 to 4 carbon atoms, and/or optionally substituted perbenzoic acid. Suitable substances are those which bear the O- and/or N-acyl groups of the stated number of carbon atoms and/or optionally substituted benzoyl groups. Preference is given to polyacylated alkylenediamines, especially tetraacetylethylenediamine (TAED), acylated triazine derivatives, especially 1,5-diacetyl-2,4-dioxohexahydro-1,3,5-triazine (DADHT), acylated glycolurils, especially tetraacetylglycoluril (TAGU), N-acylimides, especially N-nonanoylsuccinimide (NOSI), acylated phenolsulfonates, especially nonanoyl- or isononanoyloxybenzenesulfonate (n- or iso-NOBS), carboxylic anhydrides, especially phthalic anhydride, acylated polyhydric alcohols, especially triacetin, ethylene glycol diacetate and 2,5-diacetoxy-2,5-dihydrofuran. In addition to the conventional bleach activators or in their stead, it is also possible for what are called bleach catalysts to be incorporated into the textile treatment compositions. These substances are bleach-boosting transition metal salts or transition metal complexes, for example Mn-, Fe-, Co-, Ru- or Mo-salen complexes or -carbonyl complexes. Also usable as bleach catalysts are Mn, Fe, Co, Ru, Mo, Ti, V and Cu complexes with nitrogen-containing tripod ligands, and Co-, Fe-, Cu- and Ru-amine complexes.

Thickeners

A liquid washing and cleaning composition may comprise a thickener. The thickener may likewise be encapsulated in accordance with the invention and comprises, for example, polyacrylate thickener, xanthan gum, gellan gum, guar seed flour, alginate, carrageenan, carboxymethyl cellulose, bentonite, wellan gum, carob seed flour, agar agar, tragacanth, gum arabic, pectin, polyose, starch, dextrin, gelatin and casein. Other usable thickeners are modified natural substances such as modified starches and celluloses, examples here being carboxymethyl cellulose and other cellulose ethers, hydroxyethyl and -propyl cellulose, and seed flour ethers.

The polyacrylic and polymethacrylic thickeners include, for example, the high molecular weight homopolymers of acrylic acid crosslinked with a polyalkenyl polyether, especially an allyl ether of sucrose, pentaerythritol or propylene (INCI name according to the International Dictionary of Cosmetic Ingredients from The Cosmetic, Toiletry and Fragrance Association (CTFA): Carbomer), which are also referred to as carboxyvinyl polymers. Such polyacrylic acids are available inter alia from 3V Sigma under the Polygel® trade name, e.g. Polygel DA, and from B. F. Goodrich under the Carbopol® trade name, e.g. Carbopol 940 (molecular weight about 4 000 000 g/mol), Carbopol 941 (molecular weight about 1 250 000 g/mol) or Carbopol 934 (molecular weight about 3 000 000 g/mol). In addition, these include the following acrylic acid copolymers: (i) copolymers of two or more monomers from the group of acrylic acid, methacrylic acid and its simple esters formed preferably with C1-4 alkanols (INCI Acrylates Copolymer), which include for instance the copolymers of methacrylic acid, butyl acrylate and methyl methacrylate (CAS name according to Chemical Abstracts Service: 25035-69-2) or of butyl acrylate and methyl methacrylate (CAS 25852-37-3) and which are available for example from Rohm and Haas under the Aculyn® and Acusol® trade names, and also from Degussa (Goldschmidt) under the Tego® Polymer trade name, for example the anionic nonassociative polymers Aculyn 22, Aculyn 28, Aculyn 33 (crosslinked), Acusol 810, Acusol 820, Acusol 823 and Acusol 830 (CAS 25852-37-3); (ii) crosslinked high molecular weight acrylic acid copolymers, which include for instance the copolymers, crosslinked with an allyl ether of sucrose or of pentaerythritol, of C10-30 alkyl acrylates with one or more monomers from the group of acrylic acid, methacrylic acid and their simple esters, formed preferably with C1-4 alkanols (INCI Acrylates/C10-30 Alkyl Acrylate Crosspolymer) and which are available for example from B. F. Goodrich under the Carbopol® trade name, e.g. the hydrophobized Carbopol ETD 2623 and Carbopol 1382 (INCI Acrylates/C10-30 Alkyl Acrylate Crosspolymer), and Carbopol Aqua 30 (formerly Carbopol EX 473).

A further polymeric thickener for use with preference is xanthan gum, a microbial anionic heteropolysaccharide which is produced from *Xanthomonas campestris* and a few other species under aerobic conditions and has a molar mass of 2 to 15 million g/mol. Xanthan is formed from a chain having beta-1,4-bonded glucose (cellulose) with side chains. The structure of the subgroups consists of glucose, mannose, glucuronic acid, acetate and pyruvate, and the number of pyruvate units determines the viscosity of the xanthan gum. Another useful thickener is especially a fatty alcohol. Fatty alcohols may be branched or unbranched and of native origin or petrochemical origin. Preferred fatty alcohols have a carbon chain length of 10 to 20 carbon atoms, preferably 12 to 18. Preference is given to using mixtures of different carbon chain lengths, such as tallow fat alcohol or coconut fat alcohol. Examples are Lorol® Spezial (C12-14-ROH) or Lorol® Technisch (C12-18-ROH) (both from Cognis). Preferred liquid washing and cleaning compositions contain, based on the overall composition, 0.01% to 3% by weight and preferably 0.1% to 1% by weight of thickeners. The amount of thickener used is dependent on the type of thickener and the desired degree of thickening.

Enzymes

The washing and cleaning compositions may comprise enzymes in encapsulated form and/or directly in the washing and cleaning compositions. Useful enzymes are especially those from the classes of the hydrolases, such as the proteases, esterases, lipases or lipolytic enzymes, amylases, cellulases or other glycosyl hydrolases, hemicellulase, cutinases, beta-glucanases, oxidases, peroxidases, perhydrolases and/or laccases and mixtures of said enzymes. All these hydrolases contribute in the wash to the removal of stains such as protein-, grease- or starch-containing stains and gray discoloration. Cellulases and other glycosyl hydrolases can additionally contribute to color retention and to increasing the softness of the textile as a result of the removal of pilling and microfibrils. Oxidoreductases can also be used for bleaching and/or for inhibiting dye transfer. Of particularly good suitability are enzymatic active ingredients obtained from bacteria strains or fungi such as *Bacillus subtilis, Bacillus licheniformis, Streptomyceus griseus* and *Humicola insolens*. Preference is given to using proteases of the subtilisin type and especially proteases which are obtained from *Bacillus lentus*. Of particular interest are enzyme mixtures, for example of protease and amylase or protease and lipase or lipolytic enzymes or protease and cellulase or of cellulase and lipase or lipolytic enzymes or of protease, amylase and lipase or lipolytic enzymes or protease, lipase or lipolytic enzymes and cellulase, but especially protease and/or lipase-containing mixtures or mixtures with lipolytic enzymes. Examples of such lipolytic enzymes are the known cutinases. Peroxidases or oxidases have also been found to be suitable in some cases. Suitable amylases especially include alpha-amylases, isoamylases, pullulanases and pectinases. Cellulases used are preferably cellobiohydrolases, endoglucanases and p-glucosidases, which are also called cellobiases, or mixtures of these. Since different cellulase types differ by virtue of their CMCase and avicelase activities, the desired activities can be established through specific mixtures of the cellulases.

The enzymes can be adsorbed onto carriers in order to protect them from premature decomposition. The fraction of the enzymes, of the enzyme liquid formulation(s) or of the enzyme granules directly in washing and cleaning compositions may, for example, be about 0.01% to 5% by weight, preferably 0.12% to about 2.5% by weight.

However, it may also be preferable, for example in the case of special washing and cleaning compositions for consumers having allergies, for the washing and cleaning composition to contain no enzymes.

Electrolytes

Electrolytes used from the group of the inorganic salts may be a wide range of very different salts. Preferred cations are the alkali metal and alkaline earth metals; preferred anions are the halides and sulfates. From a production point of view, the use of NaCl or $MgCl_2$ in the washing and cleaning compositions is preferred. The proportion of electrolytes in the washing and cleaning compositions is typically 0.1% to 5% by weight.

Optical Brighteners

Optical brighteners (called "whiteners") can be added to the washing and cleaning compositions in order to eliminate graying and yellowing of the treated textile fabrics. These substances become attached to the fibers and bring about a lightening and simulated bleaching effect by converting invisible ultraviolet radiation to visible long-wave light, the ultraviolet light absorbed from the sunlight being emitted as slightly bluish fluorescence and producing pure white with the yellow shade of the grayed or yellowed laundry. Suitable compounds that can be encapsulated in accordance with the invention come for example from the substance classes of the 4,4'-diamino-2,2'-stilbenedisulfonic acids (flavone acids), 4,4'-distyrylbiphenyls, methylumbelliferones, coumarins, dihydroquinolinones, 1,3-diarylpyrazolines, naphthalimides, benzoxazole, benzisoxazole and benzimidazole systems, and also the pyrene derivatives substituted by heterocycles. The optical brighteners are usually used in amounts between 0% and 0.3% by weight, based on the finished washing and cleaning composition.

Graying Inhibitors

Graying inhibitors have the task of keeping the dirt detached from the fibers suspended in the liquor and hence of preventing reattachment of the dirt. Suitable for this purpose are water-soluble colloids, usually organic in nature, for example size, gelatin, salts of ethersulfonic acids of starch or of cellulose or salts of acidic sulfuric acid esters of cellulose or of starch.

Anticrease Agents

Since textile fabrics, especially made of rayon, spun rayon, cotton and mixtures thereof, can have a tendency to crease because the individual fibers are sensitive to bending, folding, pressing and squashing transverse to the fiber direction, the washing and cleaning compositions may contain synthetic anticrease agents that are encapsulated in accordance with the invention. These include, for example, synthetic products based on fatty acids, fatty acid esters, fatty acid amides, fatty acid alkylol esters, fatty acid alkylolamides or fatty alcohols, which have usually been reacted with ethylene oxide, or products based on lecithin or modified phosphoric acid esters.

Active Antimicrobial Ingredients

To control microorganisms, the washing and cleaning compositions may contain encapsulated active antimicrobial ingredients. A distinction is made here, according to the antimicrobial spectrum and mechanism of action, between bacteriostats and bactericides, fungistats and fungicides, etc. Important substances from these groups are, for example, benzalkonium chlorides, alkylarylsulfonates, halophenols and phenylmercuric acetate.

Antioxidants

In order to prevent unwanted changes to the washing and cleaning compositions and/or the treated textile fabrics caused by the action of oxygen and other oxidative processes, the washing and cleaning compositions may contain antioxidants that are encapsulated in accordance with the invention. This compound class includes, for example, substituted phenols, hydroquinones, catechols and aromatic amines, and also organic sulfides, polysulfides, dithiocarbamates, phosphites, phosphonates and vitamin E.

Foam Inhibitors

To improve the rewettability of the treated textile fabrics and to facilitate ironing of the treated textile fabrics, silicone derivatives, for example, can be used in the textile treatment compositions. These additionally improve the rinse-out performance of the washing and cleaning compositions by virtue of their foam-inhibiting properties. Preferred silicone derivatives are, for example, polydialkyl- or alkylarylsiloxanes in which the alkyl groups have one to five carbon atoms and have been entirely or partly fluorinated. Preferred silicones are polydimethylsiloxanes, which may optionally have been derivatized and are then amino-functional or quaternized and/or have Si—OH, Si—H and/or Si—Cl bonds. The viscosities of the preferred silicones at 25° C. are in the range between 100 and 100 000 mPas, where the silicones may be used in amounts between 0.2% and 5% by weight, based on the overall washing and cleaning composition.

UV Absorbers

Finally, the washing and cleaning compositions may also contain UV absorbers, which become attached to the treated textile fabrics and improve the light resistance of the fibers. Compounds which have these desired properties can be encapsulated in accordance with the invention and are, for example, the compounds effective as a result of radiationless deactivation and derivatives of benzophenone having substituents in the 2 and/or 4 position. Additionally suitable are also substituted benzotriazoles, 3-phenyl-substituted acrylates (cinnamic acid derivatives), optionally with cyano groups in the 2 position, salicylates, organic nickel complexes, and natural products such as umbelliferone and endogeneous urocanic acid.

Heavy Metal Complexing Agents

In order to avoid the decomposition of certain washing composition ingredients catalyzed by heavy metals, it is possible to use substances which complex heavy metals. Suitable heavy metal complexing agents that are encapsulated in accordance with the invention are, for example, the alkali metal salts of ethylenediaminetetraacetic acid (EDTA) or of nitrilotriacetic acid (NTA), and also alkali metal salts of anionic polyelectrolytes such as polymaleates and polysulfonates. A preferred class of complexing agents is that of the phosphonates, which are present in preferred textile treatment compositions in amounts of 0.01% to 2.5% by weight, preferably 0.02% to 2% by weight and especially of 0.03% to 1.5% by weight. These preferred compounds especially include organophosphonates, for example 1-hydroxyethane-1,1-diphosphonic acid (HEDP), aminotri(methylenephosphonic acid) (ATMP), diethylenetriaminepenta (methylenephosphonic acid) (DTPMP or DETPMP), and 2-phosphonobutane-1,2,4-tricarboxylic acid (PBS-AM), which are usually used in the form of their ammonium or alkali metal salts.

Cosmetic Formulations

The capsules of the invention are especially suitable for introduction of active ingredients and substances into cosmetic products (especially personal care products) and/or pharmaceutical compositions. Preference is given here to the perfume oils, aromas, aroma substances, fragrances.

It is preferably possible to encapsulate active therapeutic ingredients in the capsules of the invention. Cosmetic products and pharmaceutical compositions preferably comprise a number of auxiliaries and additives. These auxiliaries and additives may, as necessary, also be encapsulated into the capsules of the invention. The typical auxiliaries and additives which may be present in cosmetic products and/or pharmaceutical compositions and which can also be encapsulated in the capsules of the invention are, for example, mild surfactants, oil bodies, emulsifiers, pearlescent waxes, coolants, bodying agents, thickeners, superfatting agents, stabilizers, polymers, silicone compounds, fats, waxes, lecithins, phospholipids, UV light protection factors, humectants, active biogenic ingredients, antioxidants, deodorants, antiperspirants, antidandruff agents, film formers, swelling agents, insect repellents, self-tanning agents, tyrosine inhibitors (depigmenting agents), hydrotropes, solubilizers, preservatives, perfume oils, dyes and the like.

Especially active ingredients such as active cooling ingredients are suitable for encapsulation into the capsules of the invention. What is advantageous in the case of such an encapsulation is that the cooling, for example in the case of creams, pastes, sprays etc., sets in only on use, i.e. when rubbed on the skin. The capsules of the invention are particularly suitable in the case of such a use, for example as aftersun creme or aftersun sprays.

Oil Bodies

Examples of useful oil bodies include Guerbet alcohols based on fatty alcohols having 6 to 18, preferably 8 to 10, carbon atoms, esters of linear $C_6$-$C_{22}$ fatty acids with linear or branched $C_6$-$C_{22}$ fatty alcohols or esters of branched $C_6$-$C_{13}$ carboxylic acids with linear or branched $C_6$-$C_{22}$ fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostea rate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Additionally suitable are esters of linear $C_6$-$C_{22}$ fatty acids with branched alcohols, especially 2-ethylhexanol, esters of $C_{18}$-$C_{38}$-alkylhydroxycarboxylic acids with linear or branched $C_6$-$C_{22}$ fatty alcohols, especially Dioctyl Malate, esters of linear and or branched fatty acids with polyhydric alcohols (for example propylene glycol, dimer diol or trimer triol) and/or Guerbet alcohols, triglycerides based on $C_6$-$C_{10}$ fatty acids, and liquid mono-/di-/triglyceride mixtures based on $C_6$-$C_{18}$ fatty acids, esters of $C_6$-$C_{22}$ fatty alcohols and/or Guerbet alcohols with aromatic carboxylic acids, especially benzoic acid, esters of $C_2$-$C_{12}$ dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$ fatty alcohol carbonates, for example Dicaprylyl Carbonate (Cetiol® CC), Guerbet carbonates based on fatty alcohols having 6 to 18, preferably 8 to 10, C atoms, esters of benzoic acid with linear and or branched $C_6$-$C_{22}$ alcohols (e.g. Finsolv® TN), linear or branched, symmetric or unsymmetric dialkyl ethers having 6 to 22 carbon atoms per alkyl group, for example Dicaprylyl Ether (Cetiol® OE), ring-opening products of epoxidized fatty acid esters with polyols, silicone oils (cyclomethicone, silicomethicone types inter alia) and/or aliphatic or naphthenic hydrocarbons, for example such as squalane, squalene or dialkylcyclohexanes in consideration.

Fats and Waxes

Typical examples of fats are glycerides, i.e. solid or liquid, vegetable or animal products consisting essentially of mixed glycerol esters of higher fatty acids; useful waxes include natural waxes, for example candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microwaxes; chemically modified waxes (hard waxes), for example montan ester waxes, Sasol waxes, hydrogenated jojoba waxes and synthetic waxes, for example polyalkylene waxes and polyethylene glycol waxes. As well as the fats, useful additives are also fatlike substances such as lecithins and phospholipids. The term "lecithins" is understood by the person skilled in the art to mean those glycerophospholipids that form from fatty acids, glycerol, phosphoric acid and choline by esterification. Lecithins are therefore frequently also referred to among specialists as phosphatidylcholines (PC). Examples of natural lecithins include the cephalins, which are also referred to as phosphatidic acids, and are derivatives of 1,2-diacyl-sn-glycerol-3-phosphoric acids. By contrast, phospholipids are usually understood to be mono- and preferably diesters of phosphoric acid with glycerol (glycerol phosphate), which are generally included among the fats. In addition, sphingosines or sphingolipids are also useful.

Pearlescent Waxes

Examples of useful pearlescent waxes include: alkylene glycol esters, especially ethylene glycol distearate; fatty acid alkanolamides, especially coconut fatty acid diethanolamide; partial glycerides, especially stearic acid monoglyceride; esters of polybasic, optionally hydroxy-substituted carboxylic acids with fatty alcohols having 6 to 22 carbon atoms, especially long-chain esters of tartaric acid; fatty substances, for example fatty ketones, fatty aldehydes, fatty ethers and fatty carbonates having a sum total of at least 24 carbon atoms, especially laurone and distearyl ether.

Coolants

Coolants are compounds that generate a feeling of coldness on the skin. In general, these are menthol compounds which—as well as the parent compound menthol itself—are selected, for example, from the group formed by menthol methyl ether, menthone glyceryl acetal (FEMA GRAS 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl N-ethyloxamate, monomethyl succinate (FEMA GRAS 3810), monomethyl glutamate (FEMA GRAS 4006), menthoxy-1,2-propanediol (FEMA GRAS 3784), menthoxy-2-methyl-1,2-propanediol (FEMA GRAS 3849) and the menthanecarboxylic esters and -carboxamides WS-3, WS-4, WS-5, WS-12, WS-14 and WS-30, and mixtures thereof.

A first important representative of these substances is monomenthyl succinate (FEMA GRAS 3810). Both the succinate and the analogous monomenthyl glutarate (FEMA GRAS 4006) are important representatives of monomenthyl esters based on di- and polycarboxylic acids:

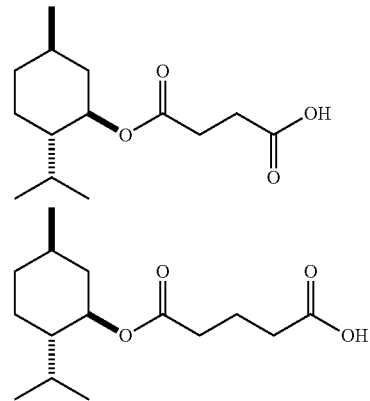

Examples of uses of these substances can be found, for example, in publications WO 2003 043431 (Unilever) or EP 1332772 A1 (IFF).

The next important group of menthol compounds that are preferred in accordance with the invention includes carbonate esters of menthol and polyols, for example glycols, glycerol or carbohydrates, for example menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives. Preference is likewise given to the menthol compounds menthyl lactate (FEMA GRAS 3748=Frescolat® ML) and especially menthone glyceryl acetal (FEMA GRAS 3807) or menthone glyceryl ketal (FEMA GRAS 3808), which is marketed under the Frescolat® MGA name. Very particularly advantageous substances among these have been found to be menthone glyceryl acetal/ketal, menthyl lactate, menthol ethylene glycol carbonate and menthol propylene glycol carbonate, which are sold by the applicant under the Frescolat® MGA, Frescolat® ML, Frescolat® MGC and Frescolat® MPC names.

The 1970s saw the first development of menthol compounds having a C—C bond in the 3 position, a number of representatives of which can likewise be used. These substances are generally referred to as WS types. The parent compound is a menthol derivative in which the hydroxyl group has been replaced by a carboxyl group (WS-1). All other WS types derive from this structure, for example the preferred species WS-3, WS-4, WS-5, WS-12, WS-14 and WS-30.

Bodying Agents and Thickeners

Useful bodying agents are primarily fatty alcohols or hydroxy fatty alcohols having 12 to 22 and preferably 16 to 18 carbon atoms and additionally partial glycerides, fatty acids or hydroxy fatty acids. Preference is given to a combination of these substances with alkyl oligoglucosides and/or fatty acid N-methylglucamides of the same chain length and/or polyglycerol poly-12-hydroxystearates. Suitable thickeners are, for example, Aerosil types (hydrophilic silicas), polysaccharides. Bentonites have also been found to be particularly effective, for example Bentone® Gel VS-5PC (Rheox), which is a mixture of cyclopentasiloxane, disteardimonium hectorite and propylene carbonate. Also useful are surfactants, for example ethoxylated fatty acid glycerides, esters of fatty acids with polyols, for example pentaerythritol or trimethylolpropane, fatty alcohol ethoxylates with a narrow global distribution or alkyl oligoglucosides, and electrolytes such as sodium chloride and ammonium chloride.

Superfatting Agents and Stabilizers

Superfatting agents used may be substances, for example lanolin and lecithin, and polyethoxylated or acrylated lanolin and lecithin derivatives, polyol fatty acid esters, monoglycerides and fatty acid alkanolamides, where the latter simultaneously serve as foam stabilizers.

UV Light Protection Factors

UV light protection factors are understood to mean, for example, organic substances that are in liquid or crystalline form at room temperature (light protection filters), which are capable of absorbing ultraviolet rays and releasing the energy absorbed again in the form of longer-wave radiation, for example heat. The UV light protection factors are typically present in amounts of 0.1% to 5% and preferably 0.2% to 1% by weight. UVB filters may be oil-soluble or water-soluble. Examples of oil-soluble substances include:

3-benzylidenecamphor or 3-benzylidenenorcamphor and derivatives thereof, for example 3-(4-methylbenzylidene)camphor described;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-nnethoxycinnannate, 2-ethylhexyl 2-cyano-3,3-phenylcinnamate (Octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-nn-ethylbenzophenone, 2,2'-dihydroxy-4-methoxybenzophenone;

esters of benzmalonic acid, preferably di-2-ethylhexyl 4-methoxybenzmalonate;

triazine derivatives, for example 2,4,6-trianilino-(p-carbo-2'-ethyl-1'-hexyloxy)-1,3,5-triazine and Octyl Triazone or Dioctyl Butamido Triazone (Uvasorb® HEB);

propane-1,3-diones, for example 1-(4-tert-butylphenyl)-3-(4'-methoxyphenyl)-propane-1,3-dione;

ketotricyclo(5.2.1.0)decane derivatives.

Typical UV-A filters especially include derivatives of benzoylmethane, for example 1-(4'-tert-butylphenyl)-3-(4'-methoxyphenyl)propane-1,3-dione, 4-tert-butyl-4'-methoxydibenzoylmethane (Parsol® 1789), hexyl 2-(4-diethylamino-2-hydroxybenzoyl)-benzoate (Uvinul® A Plus), 1-phenyl-3-(4'-isopropylphenyl)propane-1,3-dione and enamine compounds. The UV-A and UV-B filters may of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (Octocrylene) in combination with esters of cinnamic acid, preferably 2-ethylhexyl 4-methoxycinnamate and/or propyl 4-methoxycinnamate and/or isoamyl 4-methoxycinnamate.

As well as the soluble substances mentioned, insoluble light protection pigments are also useful for this purpose, namely finely dispersed metal oxides or salts. Examples of suitable metal oxides are especially zinc oxide and titanium dioxide, and additionally oxides of iron, zirconium, silicon, manganese, aluminum and cerium and mixtures thereof. Salts used may be silicates (talc), barium sulfate or zinc stearate. The oxides and salts are used in the form of pigments for skincare and skin protection emulsions and decorative cosmetics. The particles here should have an average diameter of less than 100 nm, preferably between 5 and 50 nm and especially between 15 and 30 nm. They may have a spherical shape, but it is also possible to use particles that have an ellipsoidal shape or one that deviates in some other way from the spherical form. The pigments may also be in surface-treated, i.e. hydrophilized or hydrophobized, form. Typical examples are coated titanium dioxides, for example titanium dioxide T 805 (Degussa) or Eusolex® T2000, Eusolex® T, Eusolex® T-ECO, Eusolex® T-S, Eusolex® T-Aqua, Eusolex® T-45D (all Merck), Uvinul TiO$_2$ (BASF). Useful hydrophobic coating agents include, in particular, silicones and especially trialkoxyoctylsilanes or simethicone. In sunscreens, preference is given to using what are called micro- or nanopigments. Preference is given to using micronized zinc oxide, for example Z-COTE® or Z-COTE HP1®.

Active Biogenic Ingredients and Antioxidants

Active biogenic ingredients are understood to mean, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract and vitamin complexes.

Antioxidants interrupts the photochemical reaction chain which is triggered when UV radiation penetrates into the skin. Typical examples of these are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximine, homocysteine sulfoximine, buthionine sulfone, penta-, hexa-, heptathionine sulfoximine) in very small acceptable dosages (e.g. pmol to µmol/kg), and also (metal) chelators (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbylphosphate, ascorbyl acetate), tocopherols and derivatives (e.g. vitamin E acetate), vitamin A and derivatives (vitamin A palmitate) and coniferyl benzoate from benzoin, rutic acid and derivatives thereof, α-glycosylrutine, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives that are suitable in accordance with the invention (salts, esters, ethers, sugars, nucleotides, nucleosides, peptides and lipids) of these active ingredients mentioned.

Deodorants and Microbe Inhibitors

Cosmetic deodorants counteract, mask or eliminate body odor. Body odor results from the action of skin bacteria on apocrine perspiration, forming unpleasant-spelling degradation products. Accordingly, deodorants contain active ingredients that function as microbe inhibitors, enzyme inhibitors, odor absorbers or odor maskers.

Odor Absorbers.

Suitable odor absorbers are substances that are able to absorb and largely retain odor-forming compounds. They lower the partial pressure of the individual components, thus also reducing their rate of diffusion. It is important here that perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or styrax or certain abietic acid derivatives. The odor maskers are fragrances or perfume oils, which, in addition to their function as odor maskers, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also useful are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-dannascone, geranium oil bourbon, cyclohexyl salicylate, Vertofix Coeur, Iso-E-Super, Fixolide NP, everynl, iraldein gamma, phenylacetic acid, geranyl acetate, benzyl acetate, rose oxide, romilat, irotyl and floramat alone or in mixtures.

Antiperspirants.

Antiperspirants reduce the formation of perspiration by influencing the activity of the eccrine sweat glands, thus counteracting underarm wetness and body odor. Aqueous or anhydrous formulations of antiperspirants typically comprise the following ingredients:

active astringent ingredients,
oil components,
bodying agents.

In addition, customary oil-soluble auxiliaries may be present in smaller amounts in antiperspirants. Such oil-soluble auxiliaries may be, for example:

inflammation-inhibiting, skin-protecting or pleasant-spelling essential oils,
synthetic active skin-protecting ingredients and/or
oil-soluble perfume oils.

Active Antidandruff Ingredients

Useful active antidandruff ingredients include Piroctone Olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, sulfur colloidal, sulfur polyethylene glycol sorbitan monooleate, sulfur ricinol polyethoxylate, sulfur tar distillates, salicylic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

Insect Repellents

Useful insect repellents include N,N-diethyl-m-toluamide, pentane-1,2-diol or ethyl butylacetylaminopropionate.

Constituents for Oral and Dental Care

Oral and dental care compositions are understood to mean products that serve for oral and dental cleaning and care. Examples of these are toothpastes, tooth gels and the like.

Toothpastes or tooth creams are generally understood to mean formulations in gel or paste form that are composed of water, thickeners, humectants, abrasives or cleaning bodies, surfactants, sweeteners, aromas, active deodorizing ingredients and active ingredients to counteract oral and dental disorders. In the toothpastes of the invention, it is possible to use all customary cleaning bodies, for example chalk, dicalcium phosphate, insoluble sodium metaphosphate, aluminum silicates, calcium pyrophosphate, finely divided synthetic resins, silicas, aluminum oxide and aluminum oxide trihydrate.

Cleaning bodies that are suitable with preference for the toothpastes of the invention are in particular finely divided xerogel silicas, hydrogel silicas, precipitated silicas, aluminum oxide trihydrate and finely divided alpha-aluminum oxide or mixtures of these cleaning bodies in amounts of 15% to 40% by weight of the toothpaste. Useful humectants are predominantly low molecular weight polyethylene glycols, glycerol, sorbitol or mixtures of these products in amounts up to 50% by weight. Among the known thickeners, thickening, finely divided gel silicas and hydrocolloids are suitable, for example carboxymethyl cellulose, hydroxyethyl cellulose, hydroxypropyl guar, hydroxyethyl starch, polyvinylpyrrolidone, high molecular weight polyethylene glycol, plant gums such as tragacanth, agar-agar, carrageen moss, gum arabic, xantham gum and carboxyvinyl polymers (e.g. Carbopol® types). In addition to the mixtures of menthofuran and menthol compounds, the oral and dental care compositions may especially surface-active substances, preferably anionic and nonionic high-foam surfactants, such as the substances already mentioned above, but especially alkyl ether sulfate salts, alkyl polyglucosides and mixtures thereof.

Further customary toothpaste additives are:
preservatives and antimicrobials, for example methyl, ethyl or propyl p-hydroxybenzoate, sodium sorbate, sodium benzoate, bromochlorophene, phenyl salicylate, thymol and the like;
active antiscaling ingredients, for example organophosphates such as 1-hydroxyethane-1,1-diphosphonic acid, 1-phosphonopropane-1,2,3-tricarboxylic acid and others that are known, for example, from U.S. Pat. No. 3,488,419, DE 2224430 A1 and DE 2343196 A1;
other caries inhibitors, for example sodium chloride, sodium monofluorophosphate, tin fluoride;
sweeteners, for example saccharin sodium, sodium cyclamate, sucrose, lactose, maltose, fructose or Apartam® (L-aspartyl-L-phenylalanine methyl ester), stevia extracts or sweetening constituents thereof, especially ribeaudioside;
additional aromas, for example eucalyptus oil, anise oil, fennel oil, caraway oil, methyl acetate, cinnamaldehyde, anethole, vanillin, thymol and mixtures of these and other natural and synthetic aromas;
pigments, for example titanium dioxide;
dyes;
buffer substances, for example primary, secondary or tertiary alkali metal phosphates or citric acid/sodium citrate;
wound-healing and inflammation-inhibiting substances, for example allantoin, urea, azulene, chamomile active ingredients and acetylsalicylic acid derivatives.

A preferred execution of the cosmetic formulations is toothpastes in the form of an aqueous, pasty dispersion containing polishing agents, humectants, viscosity regulators and optionally further customary components, and contain the mixture of menthofuran and menthol compounds in amounts of 0.5% to 2% by weight.

To improve the flow characteristics, it is also possible to use hydro tropes, for example ethanol, isopropyl alcohol or polyols; these substances correspond largely to the carriers outlined at the outset. Polyols that are an option here preferably have 2 to 15 carbon atoms and at least two hydroxyl groups. The polyols may also contain further functional groups, especially amino groups, or have been modified with nitrogen. Typical examples are
glycerol;
alkylene glycols, for example ethylene glycol, diethylene glycol, propylene glycol, butylene glycol, hexylene glycol and polyethylene glycols having an average molecular weight of 100 to 1000 g/mol;
industrial oligoglycerol mixtures having an intrinsic condensation level of 1.5 to 10, for instance industrial diglycerol mixtures having a diglycerol content of 40% to 50% by weight;
methylol compounds, such as, in particular, trimethylolethane, trimethylolpropane, trimethylolbutane, pentaerythritol and dipentaerythritol;
lower alkyl glucosides, especially those having 1 to 8 carbons in the alkyl radical, for example methyl and butyl glucoside;
sugar alcohols having 5 to 12 carbon atoms, for example sorbitol or mannitol,
sugars having 5 to 12 carbon atoms, for example glucose or sucrose;
amino sugars, for example glucamine;
dialcoholamines, such as diethanolamine or 2-aminopropane-1,3-diol.

Suitable preservatives are, for example, phenoxyethanol, formaldehyde solution, paraffins, pentanediol or sorbic acid and the silver complexes known by the Surfacine® name, and the further substance classes listed in annex 6, parts A and B of the Kosmetikverordnung [German Cosmetics Act].

Perfume oils include mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamon, costus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also useful are animal raw materials, for example civet and castoreum. Typical synthetic odorant compounds are products of the ester, ether, aldehyde, ketone, alcohol and hydrocarbon type. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isonnethylionone and methyl cedryl ketone, the alcohols include anethole, citronellol, eugenol, isoeugenol, geraniol, linalool, phenylethyl alcohol and terpineol, and the hydrocarbons include mainly the terpenes and balsams. However, preference is given to using mixtures of different odorants which together produce a pleasing fragrance note. Essential oils of relatively low volatility, which are usually used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnannaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-dannascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat alone or in mixtures.

Useful aromas include, for example, peppermint oil, spearmint oil, anise oil, star anise oil, caraway oil, eucalyptus oil, fennel oil, lemon oil, wintergreen oil, clove oil, menthol and the like.

Preservatives

Suitable preservatives are, for example, phenoxyethanol, formaldehyde solution, parabens, pentanediol or sorbic acid, and the silver complexes known by the Surfacine® name and the further substance classes listed in annex 6, parts A and B of the Kosmetikverordnung.

Perfume Oils, Aromas, Aroma Substances, Fragrances

Fragrances or perfume oils which are used with preference are not subject to any restrictions at all. For instance, fragrances used may be individual odorant compounds, both synthetic or natural compounds of the ester, ether, aldehyde, ketone, alcohol, hydrocarbon, acid, carboxylic ester, aromatic hydrocarbon, aliphatic hydrocarbon, saturated and/or unsaturated hydrocarbon type, and mixtures thereof. Fragrance aldehydes or fragrance ketones used may be all the customary fragrance aldehydes and fragrance ketones which are typically used to bring about a pleasant fragrance sensation. Suitable fragrance aldehydes and fragrance ketones are common knowledge to those skilled in the art. Fragrance ketones may include all ketones which can impart a desirable fragrance or a sensation of freshness. It is also possible to use mixtures of different ketones. For example, the ketone may be selected from the group consisting of buccoxime, isojasmone, methyl beta-naphthyl ketone, musk indanone, Tonalid/musk plus, alpha-damascone, beta-damascone, delta-damascone, isodamascone, damascenone, damarose, methyl dihydrojasmonate, menthone, carvone, camphor, fenchone, alpha-ionone, beta-ionone, dihydro-beta-ionone, gamma-methylionone (so-called), fleuramone, dihydrojasmone, cisjasmone, Iso-E-Super, methyl cedrenyl ketone or methyl-cedrylone, acetophenone, methylacetophenone, para-methoxyacetophenone, methyl beta-naphthyl ketone, benzylacetone, benzophenone, para-hydroxyphenylbutanone, celery ketone or livescone, 6-isopropyldecahydro-2-naphthone, dimethyloctenone, Freskomenthe, 4-(1-ethoxyvinyl)-3,3,5,5-tetramethylcyclohexanone, methylheptenone, 2-(2-(4-methyl-3-cyclohexen-1-yl)propyl)cyclopentanone, 1-(p-menthen-6(2)-yl)-1-propanone, 4-(4-hydroxy-3-nnethoxyphenyl)-2-butanone, 2-acetyl-3,3-dimethylnorbornane, 6,7-dihydro-1,1,2,3,3-pentamethyl-4(5H)-indanone, 4-damascol, dulcinyl or cassione, gelsone, hexalone, isocyclemone E, methyl-cyclocitrone, methyl-lavender ketone, orivone, para-tert-butylcyclohexanone, verdone, delphone, muscone, neobutenone, plicatone, veloutone, 2,4,4,7-tetramethyloct-6-en-3-one, tetramerane, hedione and mixtures thereof. The ketones may preferably be selected from alpha-damascone, delta-damascone, isodamascone, carvone, gamma-methylionone, Iso-E-Super, 2,4,4,7-tetramethyloct-6-en-3-one, benzylacetone, beta-damascone, damascenone, methyl dihydrojasmonate, methylcedrylone, hedione and mixtures thereof.

Suitable fragrance aldehydes may be any desired aldehydes which, in the same way as for the fragrance ketones, impart a desired odor or a sensation of freshness. Again they may be individual aldehydes or aldehyde mixtures. Suitable aldehydes are, for example, melonal, triplal, ligustral, adoxal, anisaldehyde, cymal, ethylvanillin, florhydral, floralozone, helional, heliotropin, hydroxycitronellal, koavone, lauryl aldehyde, canthoxal, lyral, lilial, adoxal, anisaldehyde, cumal methylnonylacetaldehyde, citronellal, citronellyloxyacetaldehyde, cyclamen aldehyde, bourgeonal, p,t-bucinal, phenylacetaldehyde, undecylenealdehyde, vanillin; 2,6,10-trinnethyl-9-undecenal, 3-dodecen-1-al, alpha-n-amylcinnamaldehyde, 4-methoxybenzaldehyde, benzaldehyde, 3-(4-tert-butylphenyl)propanal, 2-methyl-3-(para-methoxyphenyl)propanal, 2-methyl-4-(2,6,6-trimethyl-2(1)-cyclohexen-1-yl)butanal, 3-phenyl-2-propenal, cis/trans-3,7-dimethyl-2,6-octadien-1-al, 3,7-dimethyl-6-octen-1-al, [(3,7-dimethyl-6-octenyl)oxy]acetaldehyde, 4-isopropyl benzyl aldehyde, 1,2,3,4,5,6,7,8-octahydro-8,8-dimethyl-2-naphthaldehyde, 2,4-dimethyl-3-cyclohexene-1-carboxyaldehyde, 2-methyl-3-(isopropylphenyl)propanal, decyl aldehyde, 2,6-dimethyl-5-heptenal; 4-(tricyclo[5.2.1.0$^{[2,6]}$]decylidene-8)-butanal; octahydro-4,7-methano-1H-indenecarboxaldehyde; 3-ethoxy-4-hydroxybenzaldehyde, para-ethyl-alpha,alpha-dinnethylhydrocinnannaldehyde, alpha-methyl-3,4-(methylenedioxy)-hydrocinnamaldehyde, 3,4-methylenedioxybenzaldehyde, alpha-n-hexylcinnamaldehyde, m-cymene-7-carboxaldehyde, alpha-nnethylphenylacetaldehyde, 7-hydroxy-3,7-dimethyloctanal, undecenal, 2,4,6-trimethyl-3-cyclohexene-1-carboxaldehyde, 4-(3)(4-methyl-3-pentenyl)-3-cyclohexenecarboxaldehyde, 1-dodecanal, 2,4-dimethylcyclohexene-3-carboxaldehyde, 4-(4-hydroxy-4-methylpentyl)-3-cyclohexene-1-carboxaldehyde, 7-methoxy-3,7-dimethyloctan-1-al, 2-methylundecanal, 2-methyldecanal, 1-nonanal, 1-octanal, 2,6,10-trinnethyl-5,9-undecadienal, 2-methyl-3-(4-tert-butyl)propanal, 3-(4-ethylphenyl)-2,2-dimethylpropanal, 3-(4-methoxyphenyl)-2-methylpropanal, methylnonylacetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropylphenyl)-2-methylpropan-1-al, 3-(4-ethylphenyl)-2,2-dimethylpropan-1-al, 3-(4-tert-butylphenyl)-2-methylpropanal, 3-(3,4-methylenedioxyphenyl)-2-methylpropan-1-al, 3-(4-ethylphenyl)-2,2-dimethylpropanal, 3-β-isopropylphenyl)butan-1-al, 2,6-dimethylhept-5-en-1-al, dihydrocinnamaldehyde, 1-methyl-4-(4-methyl-3-pentenyl)-3-cyclohexene-1-carboxaldehyde, 5- or 6-methoxyhexahydro-4,7-methanoindane-1- or -2-carboxyaldehyde, 3,7-dimethyloctan-1-al, 1-undecanal, 10-undecen-1-al, 4-hydroxy-3-nnethoxybenzaldehyde, 1-methyl-3-(4-methylpentyl)-3-cyclohexenecarboxaldehyde, 7-hydroxy-3,7-dimethyloctanal; trans-4-decenal, 2,6-nonadienal, para-tolylacetaldehyde; 4-nnethylphenylacetaldehyde, 2-methyl-4-(2,6,6-trimethyl-1-cyclohexen-1-yl)-2-butenal, ortho-nnethoxycinnamaldehyde, 3,5,6-trinnethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-dimethyl-3-oxa-5,9-undecadien-1-al), hexahydro-4,7-methanoindane-1-carboxaldehyde, octanal, 2-methyloctanal, alpha-methyl-4-(1-methylethyl)benzeneacetaldehyde, 6,6-dimethyl-2-norpinene-2-propionaldehyde, para-nnethylphenoxyacetaldehyde, 2-methyl-3-phenyl-2-propen-1-al, 3,5,5-trimethylhexanal, hexahydro-8,8-dimethyl-2-naphthaldehyde, 3-propylbicyclo[2.2.1]hept-5-ene-2-carbaldehyde, 9-decenal, 3-methyl-5-phenyl-1-pentanal, methylnonylacetaldehyde, 1-p-menthene-q-carboxaldehyde, citral or mixtures thereof, lilial citral, 1-decanal, n-undecanal, n-dodecanal, florhydral, 2,4-dimethyl-3-cyclohexene-1-carboxaldehyde, 4-methoxybenzaldehyde, 3-methoxy-4-hydroxybenzaldehyde, 3-ethoxy-4-hydroxybenzaldehyde, 3,4-methylenedioxybenzaldehyde and 3,4-dimethoxybenzaldehyde and mixtures thereof. As observed by way of example above, the fragrance aldehydes and fragrance ketones may have an aliphatic, cycloaliphatic, aromatic, ethylenically unsaturated structure or a combination of these structures. There may also be further heteroatoms or polycyclic structures present. The structures may have suitable substituents such as hydroxyl groups or amino groups. For further suitable fragrances, selected from aldehydes and ketones, reference is made to Steffen Arctander, published 1960 and 1969 respectively, reprinted 2000 ISBN: Aroma Chemicals Vol. 1: 0-931710-37-5, Aroma Chemicals Vol. 2: 0-931710-38-3.

Suitable odorant compounds of the ester type are, for example, benzyl acetate, phenoxyethyl isobutyrate, p-tert-butylcyclohexyl acetate, linalyl acetate, dimethylbenzyl carbinyl acetate (DMBCA), phenylethyl acetate, benzyl acetate, ethyl methyl phenylglycinate, allyl cyclohexylpropionate, styrallyl propionate, benzyl salicylate, cyclohexyl salicylate, floramate, melusate and jasmacyclate. Odorant compounds of the hydrocarbon type are, for example, terpenes such as limonene and pinene. Suitable fragrances of the ether type are, for example, benzyl ethyl ether and ambroxane. Suitable fragrance alcohols are, for example, 10-undecen-1-ol, 2,6-dimethylheptan-2-ol, 2-methylbutanol, 2-methylpentanol, 2-phenoxyethanol, 2-phenylpropanol, 2-tert-butylcyclohexanol, 3,5,5-trimethylcyclohexanol, 3-hexanol, 3-methyl-5-phenylpentanol, 3-octanol, 1-octen-3-ol, 3-phenylpropanol, 4-heptenol, 4-isopropylcyclohexanol, 4-tert-butylcyclohexanol, 6,8-dimethyl-2-nonanol, 6-nonen-1-ol, 9-decen-1-ol, alpha-methylbenzyl alcohol, alpha-terpineol, amyl salicylate, benzyl alcohol, benzyl salicylate, beta-terpineol, butyl salicylate, citronellol, cyclohexyl salicylate, decanol, dihydromyrcenol, dimethylbenzyl carbinol, dimethylheptanol, dimethyloctanol, ethyl salicylate, ethylvanillin, anethol, eugenol, geraniol, heptanol, hexyl salicylate, isoborneol, isoeugenol, isopulegol, linalool, menthol, myrtenol, n-hexanol, nerol, nonanol, octanol, para-menthan-7-ol, phenylethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol; if two or more fragrance alcohols are present, they may be selected independently of one another.

Fragrances and perfume oils may also be natural odorant mixtures, such as those obtainable from plant sources, examples being pine, citrus, jasmine, patchouli, rose or ylang-ylang oil. Likewise suitable are clary sage oil, camomile oil, clove oil, balm oil, mint oil, cinnamon leaf oil, lime blossom oil, juniper berry oil, vetiver oil, olibanum oil, galbanum oil and labdanum oil, and also orange blossom oil, neroli oil, orange peel oil and sandalwood oil. Essential oils such as angelica root oil, aniseed oil, arnica blossom oil, basil oil, bay oil, champaca flower oil, silver fir oil, silver fir cone oil, elemi oil, eucalyptus oil, fennel oil, pine needle oil, galbanum oil, geranium oil, gingergrass oil, guaiac wood oil, gurjun balsam oil, helichrysum oil, ho oil, ginger oil, iris oil, cajeput oil, sweet flag oil, camomile oil, camphor oil, cananga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, ambrette seed oil, myrrh oil, clove oil, neroli oil, niaouli oil, olibanum oil, origanum oil, palmarosa oil, patchouli oil, peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniper berry oil, wormwood oil, wintergreen oil, ylang-ylang oil, hyssop oil, cinnamon oil, cinnamon leaf oil, citronella oil, citrus oil and cypress oil.

Likewise suitable as fragrance are what are called fragrance precursors (pro-drugs). This class of compounds comprises compounds which release a desired odor molecule and/or fragrance molecule through the breaking of a chemical bond, by hydrolysis, for example. To form a fragrance precursor, typically, a desired fragrance raw material is joined chemically to a carrier, preferably a carrier of low or moderate volatility. The combination results in a less volatile and more strongly hydrophobic fragrance precursor, with better attachment to materials. The fragrance is released subsequently by breaking of the bond between the fragrance raw material and the carrier, as a result of a change in pH, for example (through perspiration during wear, for example), atmospheric humidity, heat and/or sunlight during storage or during drying on a washing line.

The fragrance raw material for use in fragrance precursors typically comprises saturated or unsaturated volatile compounds containing an alcohol, an aldehyde and/or a ketone group. The fragrance raw materials that are useful herein include any pleasingly odorous substances or mixtures of substances which have already been described above.

Particularly advantageous fragrance precursors which can be used conform to the formula (III)

$$R-C(OR^1)(OR^2)-OR^3 \qquad (III)$$

in which R is hydrogen, linear $C_1$-$C_8$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl and mixtures thereof; $R^1$, $R^2$ and $R^3$ independently are linear, branched or substituted $C_1$-$C_{20}$ alkyl; linear, branched or substituted $C_2$-$C_{20}$ alkenyl; substituted or unsubstituted, cyclic $C_3$-$C_{20}$ alkyl; substituted or substituted $C_6$-$C_{20}$ aryl, substituted or unsubstituted $C_2$-$C_{40}$ alkyleneoxy; substituted or unsubstituted $C_3$-$C_{40}$ alkyleneoxyalkyl; substituted or unsubstituted $C_6$-$C_{40}$ alkylenearyl; substituted or unsubstituted $C_6$-$C_{32}$ aryloxy; substituted or unsubstituted $C_6$-$C_{40}$ alkyleneoxyaryl; $C_6$-$C_{40}$ oxyalkylenearyl and mixtures thereof. The use of such substances, especially in (preferably water-insoluble) microcapsules, corresponds to one preferred embodiment of the invention.

Further particularly advantageous fragrance precursors which can be used are acetals or ketals, preferably conforming to the formula (IV)

$$R-C(R^1)(OR^3)-OR^2 \qquad (IV)$$

in which R is linear $C_1$-$C_{20}$ alkyl, branched $C_3$-$C_{20}$ alkyl, cyclic $C_6$-$C_{20}$ alkyl, branched cyclic $C_6$-$C_{20}$ alkyl, linear $C_2$-$C_{20}$ alkenyl, branched $C_3$-$C_{20}$ alkenyl, cyclic $C_6$-$C_{20}$ alkenyl, branched cyclic $C_6$-$C_{20}$ alkenyl, substituted or unsubstituted $C_6$-$C_{20}$ aryl and mixtures thereof; $R^1$ is hydrogen or R; $R^2$ and $R^3$ are each independently selected from the group consisting of linear $C_1$-$C_{20}$ alkyl, branched $C_3$-$C_{20}$ alkyl, cyclic $C_3$-$C_{20}$ alkyl, branched cyclic $C_6$-$C_{20}$ alkyl, linear $C_6$-$C_{20}$ alkenyl, branched $C_6$-$C_{20}$ alkenyl, cyclic $C_6$-$C_{20}$ alkenyl, branched cyclic $C_6$-$C_{20}$ alkenyl, $C_6$-$C_{20}$ aryl, substituted $C_7$-$C_{20}$ aryl and mixtures thereof. The use of such substances, especially in (preferably water-insoluble) microcapsules, corresponds to one preferred embodiment of the invention.

Further particularly advantageous fragrance precursors which can be used conform to the formula (V)

$$R^4O—C(OR^1)(OR^3)—OR^2 \quad (V)$$

in which $R^1$, $R^2$, $R^3$ and $R^4$ are each independently linear, branched or substituted $C_1$-$C_{20}$ alkyl; linear, branched or substituted $C_2$-$C_{20}$ alkenyl; substituted or unsubstituted, cyclic $C_5$-$C_{20}$ alkyl; substituted or unsubstituted $C_6$-$C_{20}$ aryl, substituted or unsubstituted $C_2$-$C_{40}$ alkyleneoxy; substituted or unsubstituted $C_3$-$C_{40}$ alkyleneoxyalkyl; substituted or unsubstituted $C_6$-$C_{40}$ alkylenearyl; substituted or unsubstituted $C_6$-$C_{32}$ aryloxy; substituted or unsubstituted $C_6$-$C_{40}$ alkyleneoxyaryl; $C_6$-$C_{40}$ oxyalkylenearyl; and mixtures thereof. The use of such substances, especially in (preferably water-insoluble) microcapsules, corresponds to one preferred embodiment of the invention.

It is particularly preferable for the odorants used to comprise silicic ester mixtures. Silicic esters are described for example by the formula (V)

$$R—(—O—Si(OR)_2)_n—OR \quad (V)$$

where each R is independently selected from the group containing H, the straight-chain or branched, saturated or unsaturated, substituted or unsubstituted $C_1$-$C_6$ hydrocarbon radicals and the fragrance alcohol radicals and/or biocide alcohol radicals, and m adopts values from the range from 1 to 20 and n adopts values from the range from 2 to 100. The silicic esters of the formulae preferably comprise at least one fragrance alcohol radical and/or biocide alcohol radical.

The silicic ester mixtures may be used in encapsulated form, but also in unencapsulated form. The effect of the presence of silicic ester mixtures is often that the fragrance impression achievable, both with regard to pleasance and intensity, can be improved still further. The fragrance impression is not just qualitatively better, i.e. with regard to pleasance, but also lasts longer.

The silicic ester mixtures may also be present in the microcapsules. If the silicic ester mixtures in the microcapsules make up preferably at least 2% by weight of the total amount of encapsulated odorant, % by weight based on the amount of encapsulated odorants, this is a preferred embodiment of the invention, which brings about a further improvement in the desired pleasing odor effect after drying.

Particularly suitable fragrance precursors are reaction products of compounds comprising at least one primary and/or secondary amine group, for example an amino-functional polymer, especially an amino-functional silicone, and a fragrance constituent selected from ketone, aldehyde and mixtures thereof. Useful aromas include, for example, peppermint oil, spearmint oil, anise oil, star anise oil, caraway oil, eucalyptus oil, fennel oil, lemon oil, wintergreen oil, clove oil, menthol and the like.

Aroma substances include, for example: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene phthalide, carvone, camphene, caryophyllene, cineole, cinnamyl acetate, citral, citronellol, citronellal, citronellyl acetate, cyclohexyl acetate, cymene, damascone, decalactone, dihydrocoumarin, dimethyl anthranilate, dimethyl anthranilate, dodecalactone, ethoxyethyl acetate, ethylbutyric acid, ethyl butyrate, ethyl caprate, ethyl caproate, ethyl crotonate, ethyl furaneol, ethyl guaiacol, ethyl isobutyrate, ethyl isovalerate, ethyl lactate, ethyl methyl butyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamyl isovalerate, isobutyl butyrate, isobutyraldehyde, isoeugenol methyl ether, isopropylmethylthiazole, lauric acid, levulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfurfural, 3,2,2-methylcyclopentenolone, 6,5,2-methylheptenone, methyl dihydrojasmonate, methyl jasmonate, 2-methylmethyl butyrate, 2-methyl-2-pentenolic acid, methyl thiobutyrate, 3,1-methylthiohexanol, 3-methylthiohexyl acetate, nerol, neryl acetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegone, pulegol, sinensal, sulfurol, terpinene, terpineol, terpinols, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and derivatives thereof (here preferably homofuraneol) (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethyl maltol), coumarin and coumarin derivatives, gamma-lactones (here preferably gamma-undecalactone, gamma-nonalactone, gamma-decalactone), delta-lactones (here preferably 4-methyl deltadecalactone, massoia lactone, deltadecalactone, tuberolactone), methyl sorbate, divanillin, 4-hydroxy-2(or 5)-ethyl-5(or 2)-methyl-3(2H)-furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid-n-butyl ester, n-octanoic acid ethyl ester, ethyl 3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl) disulfide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and (not explicitly stated here) stereoisomers, enantiomers, positional isomers, diastereomers, cis/trans isomers or epimers of these substances.

Preference is given to using mixtures of different fragrances (from the different fragrance classes mentioned above) which together produce a pleasing fragrance note. In this case, the total amount of the at least one fragrance is the amount of all the fragrances in the mixture together, based on the total amount of the composition.

Dyes

Dyes used may be the substances that are suitable and approved for cosmetic purposes, as compiled, for example, in the publication "Kosnnetische Färbemittel" [Cosmetic Colorants] from the Farbstoffkommission [Dyes Commission] of the Deutsche Forschungsgemeinschaft [German Research Foundation], Verlag Chemie, Weinheim, 1984, p. 81-106. Examples are Cochineal Red A (C.I. 16255), Patent Blue V (C.I. 42051), indigotin (C.I. 73015), chlorophylline (C.I. 75810), Quinoline Yellow (C.I. 47005), titanium dioxide (C.I. 77891), Indanthrene Blue RS (C.I. 69800) and madder lake (C.I.58000). Luminol may also be present as a luminescent dye. These dyes are typically used in concentrations of 0.001% to 0.1% by weight, based on the overall mixture.

In preferred embodiments, constituents of adhesives and agrochemicals have been encapsulated in the capsules of the invention.

EXAMPLES

The present invention will be more easily comprehended with reference to the examples which follow. However, these examples serve merely for illustration of the invention and cannot be interpreted in a limiting manner in relation to the scope of protection of the invention.

Example 1

Production of Microcapsules

Microcapsules were produced, once using resorcinol (KI, not in accordance with the invention), then 4-aminophenol (KII) and then 3-aminophenol (KIII) in the hardening.

This is done by stirring an aqueous mixture of 31.5 g of Lupasol PA 140 and 36.56 g of Luca roll SD and heating the mixture to 35° C. Subsequently, 180 g of a fragrance oil was added, stirring was continued and emulsification was effected for a further 30 min., and the particle size was adjusted correspondingly. Then formic acid is added until the reaction mixture has a pH of 3.0-3.7. Thereafter, the mixture is heated gradually to 60° C. (1000 rpm), and a melamine dispersion is added. Subsequently, stirring is continued for 1 h and then the mixture is heated to 80° C. An aqueous solution of an aminophenol (8.4 g of 3-aminophenol and 42 g of water) is added to the reaction mixture, and the mixture is stirred at 80° C. for 1 h. The pH is then checked and an aqueous urea solution is added and the mixture is stirred at 800-900 rpm at 80° C. for 1 h. This is followed by cooling and optional aftertreatment with sodium hydroxide solution and a thickener.

Example 2

Stability and Retention Capacity of the Capsules

The stability of the capsules produced in example 1 was determined by incorporating the capsules into a fabric softener formulation (about 15% ester quat) in a concentration of 1% and then storing this mixture at 45° C. Subsequently, with the aid of GC headspace measurements, the concentration of the odorants that had diffused into the fabric softener formulation was determined. With the aid of these results, the residual content of the perfume oil still present in the capsule was then calculated. The results are shown in table 1.

TABLE 1

Stability (%) and retention capacity results

| Assessment after | fresh | 1 w | 4 w | 8 w | 12 w | Formaldehyde concentration [ppm] |
|---|---|---|---|---|---|---|
| Standard, 100% WB | 100 | 94 | 71 | 32 | 0 | 460 |
| Standard without urea, 100% WB | 100 | 97 | 81 | 46 | 0 | 1890 |
| Resorcinol, 9.0 g after melamine | 99 | 97 | 88 | 69 | 54 | 72 |
| 3-Aminophenol, 9.0 g after melamine | 100 | 98 | 93 | 89 | 85 | 50 |
| 4-Aminophenol, 9.0 g after melamine | 100 | 83 | 38 | 0 | 0 | 232 |
| Mixture of 3-aminophenol and 4-aminophenol (10:1), 9.0 g after melamine | 100 | 85 | 60 | 40 | 32 | 105 |

Example 3

Retention Capacity of the Capsules

The retention capacity of the capsules produced in example 1 for individual fragrance compounds was likewise determined. The results are summarized in table 2:

TABLE 2

Retention capacity of the capsules (figures in %)

| Assessment after | fresh | 1 w | 4 w | 8 w | 12 w |
|---|---|---|---|---|---|
| Fragrance tested | Ethyl 2-methylbutyrate | | | | |
| 3-Aminophenol | 100 | 91 | 70 | 49 | 48 |
| 4-Aminophenol | 100 | 33 | <1 | <1 | — |
| Resorcinol | 100 | 96 | 60.6 | — | — |
| Standard * | 100 | 89 | — | — | — |
| Standard ** | 100 | 96 | 23 | — | — |
| Fragrance tested | Phenylethyl alcohol | | | | |
| 3-Aminophenol | 92 | 66 | 66 | 66 | 50 |
| 4-Aminophenol | 78 | <1 | <1 | — | — |
| Resorcinol | 88 | 3 | — | — | — |
| Standard * | 87 | — | — | — | — |
| Standard ** | 92 | — | — | — | — |
| Fragrance tested | p-Cresol methyl ether | | | | |
| 3-Aminophenol | 100 | 72 | 30 | 30 | 39 |
| 4-Aminophenol | 100 | <1 | <1 | — | — |
| Resorcinol | 100 | 71 | — | — | — |
| Standard * | 100 | 20 | — | — | — |
| Standard ** | 100 | 60 | — | — | — |
| Fragrance tested | Anisaldehyde | | | | |
| 3-Aminophenol | 100 | 79 | 78 | 77 | 60 |
| 4-Aminophenol | 91 | <1 | — | — | — |
| Resorcinol | 98 | 36 | — | — | — |
| Standard * | 95 | — | — | — | — |
| Standard ** | 98 | 27 | — | — | — |
| Fragrance tested | Phenyl acetate | | | | |
| 3-Aminophenol | 100 | 96 | 79 | 72 | 58 |
| 4-Aminophenol | 100 | 34 | <1 | — | — |
| Resorcinol | 100 | 96 | 50 | — | — |

TABLE 2-continued

Retention capacity of the capsules (figures in %)

| Assessment after | fresh | 1 w | 4 w | 8 w | 12 w |
|---|---|---|---|---|---|
| Standard * | 100 | 90 | — | — | — |
| Standard ** | 100 | 95 | — | — | — |

The fragrance mixture used which was used here was of the composition according to table 3:

TABLE 3

Fragrance mixture (figures in % by weight)

| SUBSTANCE | FRACTION |
|---|---|
| AGRUMEX HC | 6.15 |
| ALDEHYDE C 6 | 0.15 |
| ALDEHYDE C 8 | 0.08 |
| ALDEHYDE C 9 | 1.23 |
| ALDEHYDE C11 UNDECYLENIC | 3.08 |
| ALDEHYDE C12 MNA | 2.92 |
| AMAROCIT ® | 1.54 |
| AMBROCENIDE ® T 40 | 0.08 |
| ANETHOLSUPRA 21.5 CELSIUS | 0.31 |
| ANISALDEHYDE PURE | 0.62 |
| BENZALDEHYDE DD | 0.15 |
| BENZYL ACETATE | 0.62 |
| CALONE | 0.08 |
| CASSIX 150 | 0.15 |
| CITRONELLYL PROPIONATE | 0.15 |
| COUMARIN | 0.62 |
| CYCLABUTE | 1.54 |
| CYMOL PARA SUPRA | 1.08 |
| DAMASCONE DELTA | 0.77 |
| DECENAL TRANS-2 | 0.31 |
| DYNASCONE | 0.15 |
| ETHYL BUTYRATE | 0.15 |
| ETHYL HEPTYLATE | 3.08 |
| ETHYL 2-METHYLBUTYRATE | 4.62 |
| EUCALYPTOL NAT. | 1.85 |
| GALBASCONE | 0.15 |
| HELIOTROPIN/PIPERONAL | 0.15 |
| HERBAFLORAT | 3.08 |
| HEXYLCINNAMALDEHYDE ALPHA | 0.77 |
| IONONE BETA | 0.23 |
| ISO E SUPER | 0.77 |
| ISOBORNYL ACETATE | 18.00 |
| CAMPHOR DL | 2.31 |
| KOAVONE | 0.31 |
| CRESOL METHYL ETHER PARA | 3.08 |
| LIGUSTRAL | 1.54 |
| MANZANATE | 0.38 |
| NECTARYL | 4.62 |
| NEROLIN YARA YARA CRYST. | 1.85 |
| ORANGE OIL BRAZ. | 3.08 |
| ORYCLON ® SPECIAL | 13.85 |
| PEONILE | 0.92 |
| PHARAONE 10% DPG | 0.15 |
| PHENYLETHYL ACETATE | 0.15 |
| PHENYLETHYL ALCOHOL | 2.31 |
| ROSE OXIDE L | 0.08 |
| STYRENYL ACETATE | 2.31 |
| TERPINENE GAMMA | 0.23 |
| TERPINEOL PURE | 0.31 |
| TETRAHYDROLINALOOL | 6.15 |
| UNDECENAL TRANS-2 | 0.23 |
| VERTOCITRAL | 1.54 |

The invention claimed is:

1. A process for producing a microcapsule, comprising the following steps:
   A) providing a pre-emulsion comprising a stabilizer and a wall former, and an active ingredient to be encapsulated;
   B) initiating condensation by altering temperature and/or pH, optionally by adding alcohol or salting-out;
   C) post-hardening, by adding
      (c1) a dispersion containing at least one urea derivative or melamine derivative, and
      (c2) aminophenol component (Ia) and/or (Ib),

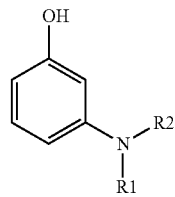
(Ia)

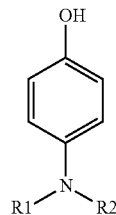
(Ib)

in which R1 and R2 independently represent hydrogen, methyl or ethyl, at temperatures of 50° C. to 100° C.;
   D) adding urea;
   E) cooling the reaction mixture obtained from step (D); and optionally
   F) spray-drying or spray-pelletizing the microcapsule thus obtained, wherein
the active ingredient is a fragrance or perfume oil, and
the at least one urea derivative or melamine derivative (i) is selected from the group consisting of 2,4,6-triamino-1,3,5-triazine (melamine) or tetrahydroimidazo[4,5-d]imidazole-2,5(1H,3H)-dione (glycoluril), benzoguanamine, acetoguanamine, adipoguanamine, glutaroguanamine, and mixtures thereof.

2. The process as claimed in claim 1, wherein said fragrance is an extract selected from the group consisting of lily, lavender, rose, jasmine, neroli, ylang-ylang, geranium, patchouli, petitgrain aniseed, coriander, cumin, juniper, bergamot, lemon, orange, mace, angelica, celery, cardamon, costus, iris, calmus, pinewood, sandalwood, guaiac wood, cedarwood, rosewood, tarragon, lemongrass, sage, thyme, spruce, fir, pine, dwarf-pine, galbanum, elemi, benzoin, myrrh, olibanum, opoponax, and mixtures thereof.

3. The process as claimed in claim 1, wherein said fragrance is selected from the group consisting of benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate, benzyl salicylate, linear alkanals having 8 to 18 carbon atoms, citral, citronellal, citronellyloxyacetaldehyde, cyclamen aldehyde, hydroxycitronellal, lilial, bourgeonal, ionones, α-isomethylionone, methyl cedryl ketone, anethole, citronellol, eugenol, isoeugenol, geraniol, linalool, phenylethyl alcohol, terpineol, terpenes, balsams, and mixtures thereof.

4. The process as claimed in claim 1, wherein said fragrance is an essential oil of low volatility selected from the group consisting of sage oil, camomile oil, oil of cloves, melissa oil, mint oil, cinnamon leaf oil, linden blossom oil, juniper berry oil, vetiver oil, olibanum oil, galbanum oil, labolanum oil, lavandin oil, and mixtures thereof.

5. The process as claimed in claim 1, wherein said fragrance is selected from the group consisting of bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat alone, and mixtures thereof.

6. A microcapsule obtained according to the process consisting of the following steps:
A) providing a pre-emulsion comprising a stabilizer and a wall former, and an active ingredient to be encapsulated;
B) initiating condensation by altering temperature and/or pH, optionally by adding alcohol or salting-out;
C) post-hardening, by adding
 (c1) a dispersion containing at least one urea derivative or melamine derivative, and
 (c2) an aminophenol component (Ia) and/or (Ib),

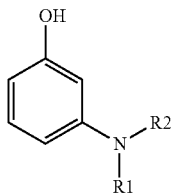

(Ia)

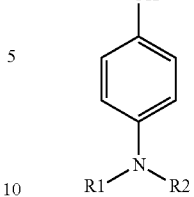

(Ib)

in which R1 and R2 independently represent hydrogen, methyl or ethyl, at temperatures of 50 to 100° C.;
D) adding urea;
E) cooling the reaction mixture obtained from step D; and optionally
F) spray-drying or spray-pelletizing the microcapsule thus obtained, wherein
the active ingredient is a fragrance or perfume oil, and
the at least one urea derivative or melamine derivative is selected from the group consisting of 2,4,6-triamino-1,3,5-triazine (melamine) or tetrahydroimidazo[4,5-d]imidazole-2,5(1H,3H)-dione (glycoluril), benzoguanamine, acetoguanamine, adipoguanamine, glutaroguanamine, and mixtures thereof.

7. Washing and cleaning compositions, cosmetic formulations or perfume compositions comprising microcapsules as claimed in claim 6.

8. Agrochemicals comprising microcapsules as claimed in claim 6.

9. Adhesives comprising microcapsules as claimed in claim 6.

* * * * *